United States Patent
Guendel et al.

(10) Patent No.: US 11,776,117 B2
(45) Date of Patent: Oct. 3, 2023

(54) MACHINE LEARNING FROM NOISY LABELS FOR ABNORMALITY ASSESSMENT IN MEDICAL IMAGING

(71) Applicant: Siemens Healthcare GmbH, Erlangen (DE)

(72) Inventors: Sebastian Guendel, Erlangen (DE); Arnaud Arindra Adiyoso, Nuremberg (DE); Florin-Cristian Ghesu, Plainsboro, NJ (US); Sasa Grbic, Plainsboro, NJ (US); Bogdan Georgescu, Princeton, NJ (US); Dorin Comaniciu, Princeton Junction, NJ (US)

(73) Assignee: Siemens Healthcare GmbH, Erlangen (DE)

(*) Notice: Subject to any disclaimer, the term of this patent is extended or adjusted under 35 U.S.C. 154(b) by 354 days.

(21) Appl. No.: 17/072,424

(22) Filed: Oct. 16, 2020

(65) Prior Publication Data
US 2022/0028063 A1     Jan. 27, 2022

Related U.S. Application Data

(60) Provisional application No. 63/054,823, filed on Jul. 22, 2020.

(51) Int. Cl.
*G06T 7/00* (2017.01)
*G06T 5/00* (2006.01)

(52) U.S. Cl.
CPC ............ *G06T 7/0012* (2013.01); *G06T 5/002* (2013.01); *G06T 2207/10116* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS 10,691,980 B1     6/2020     Guendel

FOREIGN PATENT DOCUMENTS

CN     110490880 A     11/2019

OTHER PUBLICATIONS

Jindal, Ishan, Matthew Nokleby, and Xuewen Chen. "Learning deep networks from noisy labels with dropout regularization." In 2016 IEEE 16th International Conference on Data Mining (ICDM), pp. 967-972. IEEE, 2016. (Year: 2016).*

Dgani, Yair, Hayit Greenspan, and Jacob Goldberger. "Training a neural network based on unreliable human annotation of medical images." In 2018 IEEE 15th International Symposium on Biomedical Imaging (ISBI 2018), pp. 39-42. IEEE, 2018. (Year: 2018).*

(Continued)

*Primary Examiner* — Samah A Beg

(57) ABSTRACT

For machine learning for abnormality assessment in medical imaging and application of a machine-learned model, the machine learning uses regularization of the loss, such as regularization being used for training for abnormality classification in chest radiographs. The regularization may be a noise and/or correlation regularization directed to the noisy ground truth labels of the training data. The resulting machine-learned model may better classify abnormalities in medical images due to the use of the noise and/or correlation regularization in the training.

20 Claims, 3 Drawing Sheets

(56) References Cited

OTHER PUBLICATIONS

Wang, Xiaosong, et al. "Chestx-ray8: Hospital-scale chest x-ray database and benchmarks on weakly-supervised classification and localization of common thorax diseases." Proceedings of the IEEE conference on computer vision and pattern recognition. 2017. (Year: 2017).*

Li, Lu, Yang Li, Xiangxiang Xu, Shao-Lun Huang, and Lin Zhang. "Maximal correlation embedding network for multilabel learning with missing labels." In 2019 IEEE International Conference on Multimedia and Expo (ICME), pp. 393-398. IEEE, 2019. (Year: 2019).*

Extended European Search Report (EESR) dated Dec. 10, 2021 in corresponding European patent application No. 21186575.3.

Dgani, Yair et al: "Training a neutral network based on unreliable human annotation of medical images"; 2018 IEEE 15th International Symposium On Bio Medical Imaging (ISBI 2018), IEEE, Apr. 4, 2018 (Apr. 4, 2018), pp. 39-42.

Mengying, Hu et al: "Weakly Suervised Image Calassification through Noise Regularization"; 2019 IEEE/CVF Conference On Computer Vision and Pattern Recognition (CVPR), IEEE; Jun. 15, 2019 (Jun. 15, 2019), pp. 11509-11517.

Miller, Eric et al: "A hybrid approach to imaging and anomaly characterization from dual energy CT data"; Computational Imaging IX, SPIE, 1000 20th, vol. 7873, No. 1, Feb. 10, 2011 (Feb. 10, 2011), pp. 1-11.

Gündel, Sebastian et al: "Robust classification from noisyy labels: Integrating additional knowledge for chest radiography abnormality assessment"; Medical Image Analysis, Oxford University Press, Oxford, GB; vol. 72, Apr. 24, 2021.

Görkem, Algan et al: "Image Classification with Deep Learning in the Presence of Noisy Labels. A Survey"; Arxiv. Org, Cornell University Library, 201 Olin Library Cornell University Ithaca, NY 14853; Jun. 5, 2020.

Li, Lu et al: "Maximal Correlation Embedding for Multilabel Learning with Missing Labels"; 2019 IEEE International Conference On Multimedia and Expo (ICME), IEEE; Jul. 8, 2019 (Jun. 8, 2019), pp. 393-398.

Ma, X., Wang, Y., Houle, M.E., Zhou, S., Erfani, S.M., Xia, S., Wijewickrema, S.N., & Bailey, J. (2018).Dimensionality-Driven Learning with Noisy Labels. ICML.

C. Li, C. Xu, C. Gui and M. D. Fox, "Distance Regularized Level Set Evolution and Its Application to ImageSegmentation," in IEEE Transactions on Image Processing, vol. 19, No. 12, pp. 3243-3254, Dec. 2010, doi:10.1109/TIP.2010.2069690.

Ghesu, Florin C. et al. "Quantifying and Leveraging Classification Uncertainty for Chest RadiographAssessment." MICCAI (2019).

Guendel, Sebastian & Ghesu, Florin & Grbic, Sasa & Gibson, Eli & Georgescu, Bogdan & Maier, Andreas &Comaniciu. Dorin. (2019). Multi-task Learning for Chest X-ray Abnormality Classification on Noisy Labels.

Irvin, J., Rajpurkar, P., Ko, M., Yu, Y., Ciurea-Ilcus, S., Chute, C., Marklund, H., Haghgoo, B., Ball, R.,Shpanskaya, K., et al., 2019. Chexpert: A large chest radiograph dataset with uncertainty labels and expertcomparison. arXiv preprint arXiv:1901.07031.

Jindal, Ishan & Nokleby, Matthew & Chen, Xuewen. (2016). Learning Deep Networks from Noisy Labels withDropout Regularization. 967-972. 10.1109/ICDM.2016.0121.

L. Oakden-Rayner, "Exploring the chestxray14 dataset: problems,"https://lukeoakdenrayner.wordpress.com/2017/12/18/the-chestxray14-dataset-problems/, accessed: Dec. 18, 2017.

P. Rajpurkar, J. et al. "Deep learning for chest radiograph diagnosis: A retrospective comparison of the chexnext algorithm to practicing radiologists," PLOS Medicine, vol. 15, No. 11, pp. 1-17. [Online]. Available: https://doi.org/10.1371/journal.pmed.1002686. 2018.

P. Rajpurkar, J. Irvin, K. Zhu, B. Yang, H. Mehta, T. Duan, D. Ding, A. Bagul, C. Langlotz, K. Shpanskaya et al., "Chexnet: Radiologist level pneumonia detection on chest x-rays with deep learning," arXiv:1711.05225, 2017.

Q. Guan, Y. Huang, Z. Zhong, Z. Zheng, L. Zheng, and Y. Yang, "Diagnose like a Radiologist: Attention GuidedConvolutional Neural Network for Thorax Disease Classification," ArXiv e-prints, Jan. 2016.

V. P. Gopi, Fayiz T. K and P. Palanisamy, "Regularization based CT image reconstruction using Algebraic techniques," 2014 International Conference on Electronics and Communication Systems (ICECS), Coimbatore,2014, pp. 1-3, doi: 10.1109/ECS.2014.6892689.

X. Wang, Y. Peng, L Lu, Z. Lu, M. Bagheri, and R. Summers, "Chestxray8: Hospital-scale chest x-ray databaseand benchmarks on weakly supervised classification and localization of common thorax diseases," in Proc. CVPR,2017, pp. 3462-3471.

* cited by examiner

MACHINE LEARNING FROM NOISY LABELS FOR ABNORMALITY ASSESSMENT IN MEDICAL IMAGING

RELATED APPLICATION

The present patent document claims the benefit of the filing date under 35 U.S.C. § 119(e) of Provisional U.S. Patent Application Ser. No. 63/054,823, filed Jul. 22, 2020, which is hereby incorporated by reference.

BACKGROUND

The present embodiments relate to machine learning. Machine learning algorithms have shown great promise for the computer-aided classification of medical images. For example, machine learning is used to develop automated chest radiograph systems. The assessment of chest radiographs is used for detection of thoracic diseases and abnormalities. However, developing these systems is challenging because of the high inter-rater variability in the interpretation of chest radiographs. High error rates in annotations due to the methods of annotation, e.g., natural language processing (NLP)-based methods, and inherent ambiguity in pathology appearance lead to incorrect dataset labels. These factors, in the context of machine learning-based systems, lead to overconfident systems with poor generalization on unseen data. Deep learning methods, which are known to perform well in other domains, may still be overconfident.

To correct this, higher quality, radiologist-re-annotated test sets may be used to train. Predictive uncertainty may be estimated as an orthogonal measure to the predicted abnormality probability using subjective logic. However, the label noise may still result in poor performing machine-learned models.

SUMMARY

By way of introduction, the preferred embodiments described below include methods, systems, instructions, and computer readable media for machine learning for abnormality assessment in medical imaging and application of a machine-learned model. The machine learning uses regularization of the loss, such as regularization being used for training for abnormality classification in chest radiographs. The regularization may be a noise and/or correlation regularization directed to the noisy ground truth labels of the training data. The resulting machine-learned model may better classify abnormalities in medical images due to the use of the noise and/or correlation regularization in the training.

In a first aspect, a method is provided for machine learning abnormality assessment in medical imaging by a machine. Training data including medical images and ground truth labels for the medical images is obtained. The ground truth labels designate any abnormality represented by the medical images. The machine machine trains a model from the training data. The machine training uses a loss function including a regularization. The regularization is a noise regularization and/or a correlation regularization. The model resulting from the machine training is stored in a memory.

In one embodiment, the machine training includes machine training with the loss function being a cross-entropy function comparing a classification of abnormality output of the model with the ground truth labels. Other loss functions may be used. In another embodiment, the machine training includes machine training with the ground truth labels being binary labels for absence or presence of the abnormality and the loss function being weighted as a function of number of positive and number of negative instances of the abnormality in the medical images of the training data. Other labels, such as grades or scores, may be used.

In one embodiment, the regularization of the loss function is the noise regularization. For example, a noise level of the ground truth labels is measured. The machine training includes machine training with the noise regularization being a function of the noise level. In one approach, the noise level is represented by a specificity and a sensitivity of the ground truth labels for the abnormality. The noise regularization includes a first weight that is a function of the specificity and a second weight that is a function of the sensitivity or any other measure which describes a noise ratio of the labels. The noise regularization may be any function, such as an inverse binary cross-entropy function.

In another embodiment, the ground truth labels designate at least first and second types of abnormalities. The regularization of the loss function is the correlation regularization. The correlation regularization correlates the ground truth labels for the first type of abnormality to the ground truth labels for the second type of abnormality. In one approach, the correlation regularization is a covariance. For example, at least four types of abnormalities are provided. The correlation regularization is a sum of the covariance between all of the at least four types of abnormalities.

In other embodiments, both the noise regularization and the correlation regularization are used to train.

Various types of medical images and/or abnormalities may be used. For example the medical images of the training data are chest radiographs, and the abnormalities include effusion, cardiomegaly, consolidation, atelectasis, and mass.

In application, the model resulting from the machine training is applied to a patient image for a patient. The application outputs a classification of the patient image has having or not having any abnormality.

In a second aspect, a system is provided for abnormality detection in medical imaging. A medical imaging system configured to generate an image of a patient. A processor is configured to apply a machine-learned model to the image of the patient. The machine-learned model was trained with noise and/or correlation regularization to detect an abnormality in the image. A display is configured to display a classification of the patient as having or not having the abnormality based on the detection from the application.

In one embodiment, the machine-learned model was trained with the noise regularization. The noise regularization accounts for noise in ground truth labels used in machine training. In another embodiment, the machine-learned model was trained with correlation regularization accounting for mischaracterization between different types of abnormalities.

While applicable in different medical imaging environments, the noise or correlation regularization may be for ground truth labels for abnormalities in x-ray images from an x-ray imaging system.

In a third aspect, a system is provided for machine training for abnormality classification. A memory is configured to store training data including images of anatomy and ground truth classifications for the images and to store a machine-learned classifier. A processor is configured to machine train from the training data. The machine training includes calculation of loss with a noise and/or correlation regularization. The processor is configured to machine train with the loss, resulting in the machine-learned classifier.

In one embodiment, the processor is configured to machine train with the noise regularization. In another embodiment, the processor is configured to machine train with the correlation regularization.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Machine-learning improves the generalization of abnormality classification based on label error rates assessment in chest radiography or other medical imaging. Different regularization techniques may deal with label noise, such as dropout regularization or dimensionality-driven learning strategies. Regularization may be applied in many medical imaging fields such as image reconstruction or image segmentation.

To provide robust classification from noisy labels for medical imaging abnormality assessment, regularization is applied on the classification loss. To increase the generalization accuracy of machine learning systems, regularization is applied on the classification loss. Two example regularization components are noise regularization based on the calculation of prior label noise probabilities and correlation regularization based on correlation between abnormalities. Both noise and correlation regularization lead to an improvement in terms of the generalization performance of abnormality detection and classification.

Figure 1:
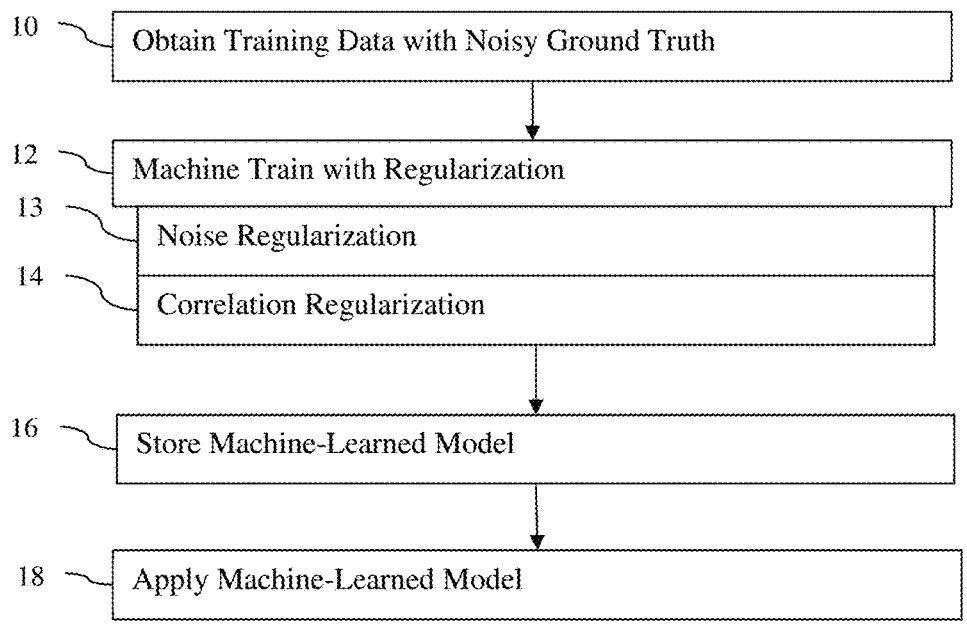
FIG. 1 is one embodiment of a method for machine training with noise and/or correlation regularization and application of a resulting machine-learned model.

FIG. 1 shows one embodiment of a method for machine learning abnormality assessment in medical imaging by a machine. In chest radiographs, regularization, such as noise, correlation, or drop-out, is used in training. For medical imaging in general (e.g., x-ray, computed tomography (CT), magnetic resonance (MR), ultrasound, single photon emission computed tomography (SPECT), and/or positron emission tomography (PET)), the regularization is at least a noise and/or correlation regularization. The noise and/or correlation regularization for medical image classification reduces the effects of noisy labels in the training data.

Figure 4:
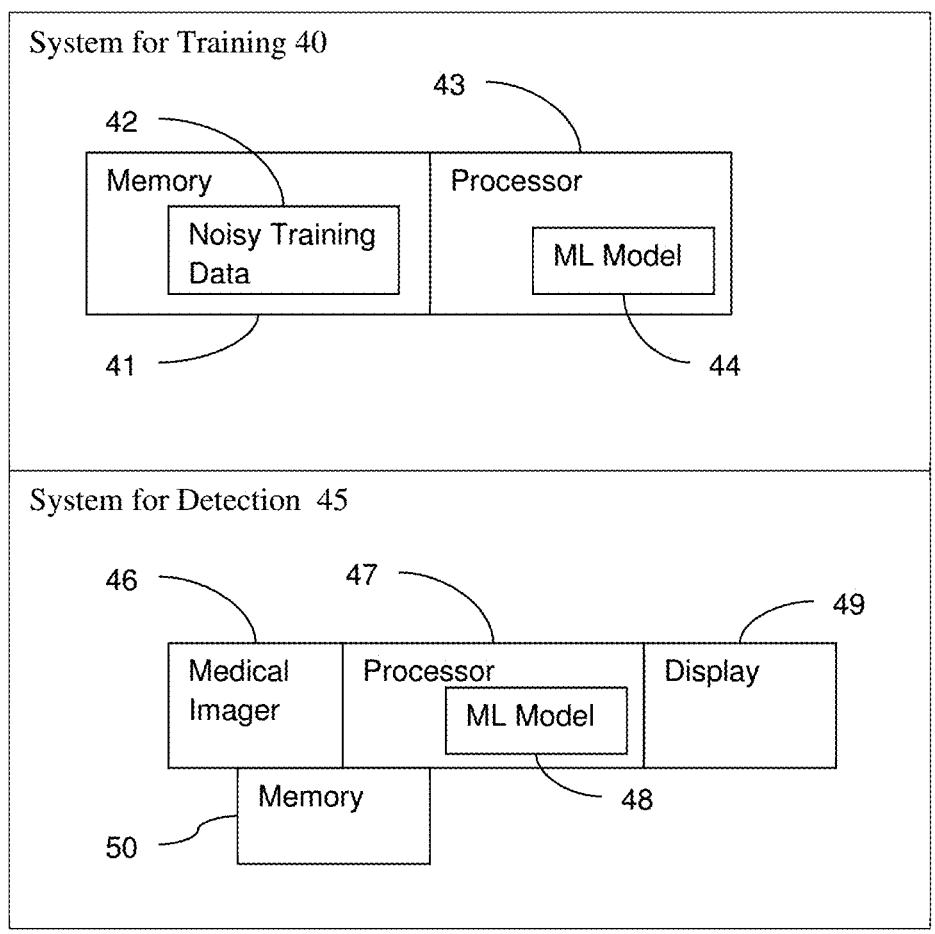
FIG. 4 is a block diagram of embodiments of systems for training using noise and/or correlation regularization and applying a trained model.

The method is implemented by the system of FIG. 4 or another system. For example, the method is implemented by the system 40 for training, including a memory 41 to store training data and the learned model and a processor 43 to perform machine training with the regularizer. Different devices may be used.

Additional, different, or fewer acts may be provided. For example, the application of act 18 and/or storage of act 16 is not provided. As another example, none of acts 13 and 14 are provided where regularization is for chest radiographs. In yet another example, only one of either act 13 or act 14 is provided. As yet another example, acts for designing an architecture of the model (e.g., layer structure of a neural network) are included.

The acts are performed in the order shown (e.g., top to bottom or numerical) or other orders. For example, act 16 may be applied after act 18. As another example, acts 13 and 14 may be performed in any order or simultaneously (e.g., where noise and correlation regularization terms are both included in the loss function).

In act 10, training data is obtained. The data is obtained by searching, data mining, loading from memory, identifying, transfer over a computer network, and/or gathering. A designer (e.g., computer scientist) obtains the training data, such as data for a particular type of medical imaging, organ of interest, disease of interest, and/or abnormality or abnormalities of interest. A computer, study, and/or database may be used to obtain the data.

The training data includes medical images. Tens, hundreds, or thousands of sample medical images are obtained. For example, x-ray radiographs from many different patients are obtained. Actual medical images from patients may be used. Alternatively, simulation of medical imaging is used to generate the medical images. In yet other embodiments, images of phantoms are used. The medical images of the training data may be from multiple sources, such as actual images of patients, simulation, and imaging of phantoms. Any sub-set of data for any domain (e.g., ultrasound, MR, CT, PET, or SPECT) may be used. Chest radiographs are used as an example herein as chest radiographs tend to have noisy ground truths and/or a large number of types of abnormalities represented in the images.

Other information may be included with the sample images. For example, clinical and/or lab results for the patients associated with the images are included. The age, weight, smoking history, blood work, and/or other information may be provided as samples with the medical images to train the classifier to detect abnormalities from input images and other types of information. In other embodiments, only medical images are used in the samples of the training data.

The training data includes ground truth labels for each of the samples. The ground truth labels are mined from patient records, indicated by a measure (e.g., application of another classifier), and/or provided by expert review of the samples. The ground truth labels are for the existence or not of the abnormality, the location of the abnormality, and/or an extent or level of the abnormality (e.g., size or score). The ground truth label is provided for each type of abnormality for each sample. For example, one chest radiograph includes a positive label for one type of abnormality and a negative label for another type of abnormality. The ground truth labels designate any abnormality represented by each of the samples (e.g., medical images).

The ground truth labels may be noisy. Some of the labels may be incorrect. Since the machine learning relies on accuracy of the ground truth labels to learn to classify whether images include abnormalities, the noisy labels introduce error in the trained classifier. The error may be due to incorrect labeling in a binary sense (e.g., abnormality X is represented or is not) and/or in an incorrect identification sense (e.g., a mass is labeled as an effusion).

The samples and labels may be for any number or types of abnormalities. For example, the labels are for a single type of abnormality (e.g., cancerous lesion). Each sample is labeled with a ground truth for whether or not the abnormality is represented in the sample. As another example, the labels are for two or more, three or more, or four or more types of abnormalities. In the chest radiograph example, the types of abnormalities include effusion, cardiomegaly, consolidation, atelectasis, and mass. Additional, different, or fewer types of abnormalities may be classified or labeled. Each sample (e.g., medical image of the training set) is labeled with one or more labels for binary or non-binary indication of representation and/or location of a respective one or more types of abnormalities.

In act 12, a machine performs machine training. A processor or computer uses the training data to machine learn. A model is defined and trained by establishing values for learnable parameters based on the training data. The samples are input and resulting outputs are compared to the ground truth labels. Through optimization (e.g., Adam), the training data is used to establish the values for the learnable parameters of the defined model that result in accurate output.

Any training may be used, such as deep learning for a neural network. A support vector machine, regression, or other machine learning and corresponding model may be used. In one embodiment, deep learning is used. Using a piecewise-differentiable function or other deep learning function, the machine trains the network to output a classification (e.g., detection or not of an abnormality) in response to an input sample (e.g., medical image). The machine trains the network through regression.

The neural network is a fully connected network (FCN) or a convolutional neural network. Other models may be used.

The defined model is trained to estimate with a loss function. Any loss function may be used, such as a cross-entropy function, L2 (e.g., least squares error), L1 distance, or other loss to obtain optimal values for the network parameters. The difference between the ground truth labels for the training images and the predictions by the model are minimized based on the measure of loss or difference by the loss function. Through optimization, the values of the learnable parameters are adjusted to minimize the loss.

The loss function includes regularization. One or more terms to regulate the loss are added. The regularizer may be a term summed with the loss. Alternatively, the regularizer is a weight or adaptive alteration in the loss calculation that accounts for the noisy labels. In one embodiment, the regularization is a noise regularization. In another embodiment, the regularization is a correlation regularization. In yet another embodiment, both the noise regularization and correlation regularization are used. Other regularizations may additionally or alternatively be used, such as drop-out regularization and/or dimensionality-driven learning.

Figure 2:
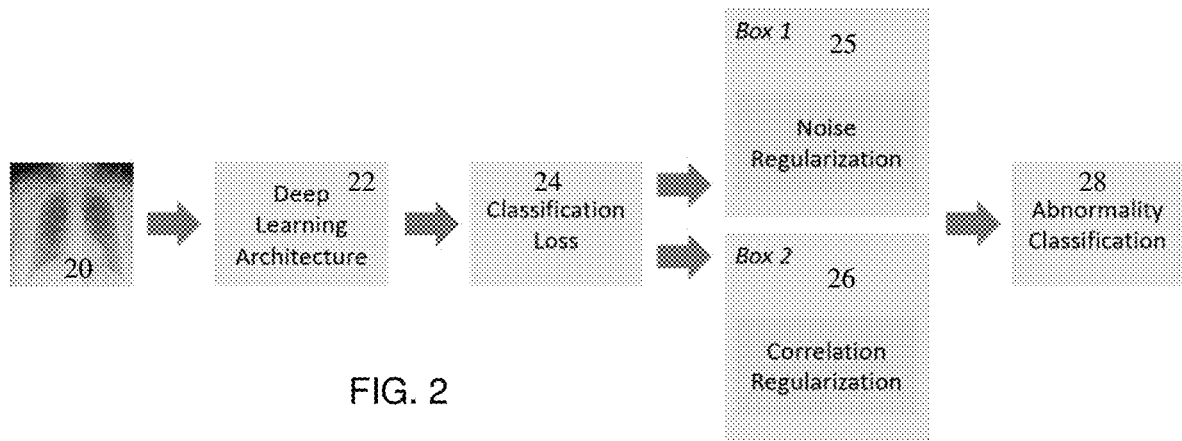
FIG. 2 illustrates an example architecture for machine training with regularization.

FIG. 2 shows an example arrangement or architecture for machine training as a pipeline. The images 20 are used as inputs to the deep learning architecture 22 (i.e., model of interrelated learnable parameters). The output of the model and the ground truth are used to determine the classification loss 24 during training. The classification loss 24 includes noise regularization 25 and/or correlation regularization 26. Once trained, the model outputs the abnormality classification 28 without loss and/or regularization. The previously used loss and regularization provides the values for the model of the architecture 22 to provide an accurate abnormality classification 28.

The ground truth labels of the training data are binary labels for the absence or presence of the abnormality in the sample, so the loss is based on binary prediction for many or all samples. In other embodiments, the labels are continuous values or have more than two discrete values, so the loss is based on accuracy along the continuum or across the discrete set.

For determining the loss, the labels are the set of $[c^{(1)} \ c^{(2)} \ \ldots \ c^{(d)}] \epsilon \{0, 1\}$ (absence or presence of the abnormality, respectively) and are compared with the network output $[p^{(1)} \ p^{(2)} \ \ldots \ p^{(d)}] \epsilon [0, 1]$. The loss is measured based on the comparison. The loss function provides the comparison.

In one embodiment to deal with an imbalance in the training data, the loss function is weighted as a function of number of positive and number of negative instances of the abnormality in the medical images of the training data. Due to the imbalanced problem (e.g., more negative than positive samples), additional weight constants $w_P^{(n)}$ and $w_N^{(n)}$ are provided for each abnormality indexed by n.

$$w_P^{(n)} = \frac{P^{(n)} + N^{(n)}}{P^{(n)}}, \text{ and } w_N^{(n)} = \frac{P^{(n)} + N^{(n)}}{N^{(n)}}$$

where $P^{(n)}$ and $N^{(n)}$ indicate the number of positive and negative cases for the entire training dataset, respectively. Integrating the weights into an example cross-entropy loss function provides:

$$\mathcal{L}_{Abn} = -\sum_{n=1}^{D} \sum_{i=1}^{F} [w_P^{(n)} c_i^{(n)} \ln(p_i^{(n)}) + w_N^{(n)} (1 - c_i^{(n)}) \ln(1 - P_i^{(n)})], \quad (1)$$

The loss is calculated based on a sum over all images or samples. The function is indexed by i, where F denotes the total number of images in the set and D denotes the total number of types of abnormalities.

For act 13, the loss function includes noise regularization. The machine training is performed with the regularization of the loss function including noise regularization. The noise level of the ground truth labels is measured and used to regularize. For example, the specificity and/or sensitivity of the ground truth labels of the training set are used to regularize.

In one embodiment, an expert reading procedure is defined. Expert radiologists read the samples and blindly re-labeled the samples. Without access to the ground truth labels and/or classification by other experts, the expert or experts classify (i.e., identify the ground truth) for each sample. The original dataset labels were not provided during the expert reading process to avoid a biased decision towards the original labels. Multiple experts may perform the reading, providing multiple instances of ground truth labels for each sample. For all cases where consensus was not reached on all labels through the independent read, an open discussion or majority vote may be carried out to establish consensus labels. Assuming that the re-defined labels are the correct labels, prior probabilities are calculated with the original and re-defined labels. Table 1 show sensitivity $s_{sens}$ and specificity $s_{spec}$ of five selected types of abnormalities for chest radiographs for the original ground truth labels verses expert re-labeling.

TABLE 1

| Abnormality | $s_{sens}$ | $s_{spec}$ |
|---|---|---|
| Effusion | 0.300 | 0.966 |
| Cardiomegaly | 0.342 | 0.986 |
| Consolidation | 0.129 | 0.949 |
| Atelectasis | 0.221 | 0.970 |
| Mass | 0.364 | 0.972 |
| Average | 0.271 | 0.969 |

Low scores indicate stronger label noise.

To incorporate the noise regularization into the loss function, a term is added to the loss function. Any regularization term may be used, such as an inverse binary cross-entropy function. The added term is a noise regularization, which is a function of the level of noise. Any function may be used. In one embodiment, two weights are added where one weight is a function of the specificity and another weight is a function of the sensitivity. In other embodiments, only sensitivity, only specificity, or another measure of noise level is used.

In one embodiment, the noise regularization as an inverse binary cross-entropy function is added to the loss function of equation 1. The resulting regularized loss function is given as:

$$\mathcal{L}_{noise} = \mathcal{L}_{Abn} + r_{noise} = -\Sigma_{n=1}^{D}\Sigma_{n=1}^{F}|w_p^{(n)}c_i^{(n)}\ln p_i^{(n)} + w_N^{(n)}(1-C_i^{(n)})\ln(1-p_i^{(n)}) + \lambda_{noise}|f_P^{(n)}w_N^{(n)}(1-c_i^{(n)})\ln p_i^{(n)} + f_N^{(n)}w_P^{(n)}c_i^{(n)}\ln(1-p_i^{(n)})\|$$ (2)

where $f_P$ and $f_N$ are the individual regularization weights for positive and negative examples. Any function using noise level may be used. In one embodiment, $f_P^{(n)} = 1 - s_{sense}$ and $f_N^{(n)} = 1 - s_{spec}$. The additional parameter $\lambda_{noise}$ is another weight to define the overall influence of the regularization term. Any value may be used for the additional parameter, such as 0.1.

The noise may be integrated into the regularization and/or loss function in a different way, such as a weight, ratio, subtraction, or use of different regularization function (e.g., L2). Instead of weights, the noise level may be integrated through addition, subtraction, or other function.

For act 14, correlation regularization is used in the loss function during machine training. The correlation regularization uses correlation of the ground truth labels for the first type of abnormality to the ground truth labels for the second type of abnormality. More strongly correlated abnormalities are more likely to be miss-classified in the ground truth labels, introducing a source of label noise.

Figure 3:
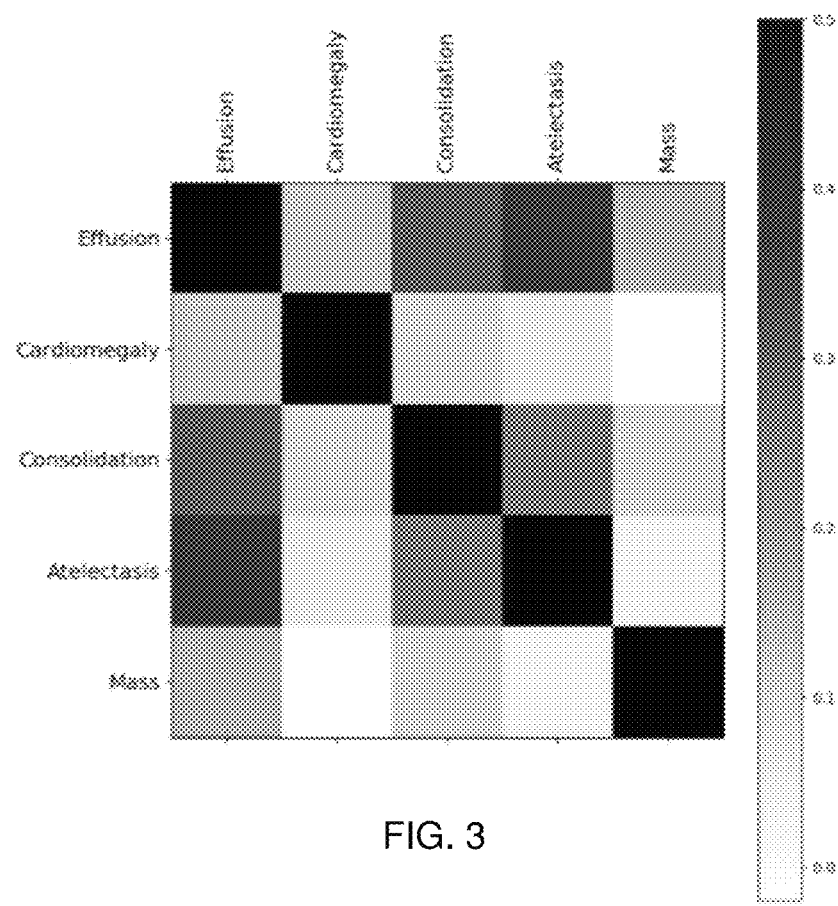
FIG. 3 shows correlation of abnormalities.

FIG. 3 shows an example in chest radiography. The strength of correlation between each abnormality is visualized. The level of correlation between each of five different types of abnormalities (effusion, cardiomegaly, consolidation, atelectasis, and mass) is shown graphically. The darker colors correspond to the level of correlation where black is full correlation (e.g., correlation coefficient is 1.0) and white is no correlation (e.g., correlation coefficient is 0.0). The correlations in these examples are 1.0 for the abnormality's correlation with itself and between 0.0 and 0.5 for correlations between different abnormalities.

The correlation regularization is based on how strongly a set of class labels $c^{(n)}$ for abnormality n correlate with a set of class labels c(r) for abnormality r where $r \in \{1 \ldots D\} \backslash \{n\}$. D denotes the number of abnormalities. Any correlation coefficient may be used as the measure of correlation. FIG. 3 uses the Pearson correlation coefficient. In other embodiments, the correlation coefficient is the covariance.

To incorporate the correlation regularization into the loss function, a term is added to the loss function. Any regularization term may be used, such as a cross-entropy function. The added term is a correlation regularization, which is a function of the levels of correlation among the different types of abnormalities to be classified. Any function may be used. In one embodiment, a sum across the different types of abnormalities of the cross-entropy weighted by the correlation coefficient is added. For example, the sum across two, three, four, or more types of abnormalities, such as the sum across five abnormalities of the example of FIG. 3, is used.

In one embodiment, the original loss function of equation 1 is adapted to consider the correlation information across all abnormalities, as represented by:

$$\mathcal{L}_{noise} = \mathcal{L}_{Abn} + r_{corr} = \Sigma_{n=1}^{D}\Sigma_{n=1}^{F}|w_p^{(n)}c_i^{(n)}\ln p_i^{(n)} + w_N^{(n)}\ln(1-p_i^{(n)}) + \lambda_{corr}\Sigma_{r \in \{1 \ldots D\} \backslash \{n\}}|conv^{(n,r)}|w_p^{(r)}c_i^{(r)})\ln p_i^{(n)} + w_N^{(r)}(1-c_i^{(r)})\ln(1-p_i^{(n)})\|$$ (3)

where $\lambda_{corr}$ is a weight (e.g., set at 1.0) and $conv^{(n, r)}$ with element (n,r) measures the covariance between the label indexed as n and the label indexed as r. Depending on the covariance matrix, all abnormality labels may influence on another given abnormality.

In other embodiments, the loss function includes two or more additional terms. For example, both noise and correlation regularization terms are included. Relative weighting may be used to control the relative contribution of the regularizers to the loss. The model is machine trained using any number of regularizers, such as the noise and correlation regularizations. Additional regularization components may be added.

Referring again to FIG. 1, the machine (e.g., processor or computer) stores the model resulting from the machine training in a memory in act 16. The model and/or copies for use by different machines may be transferred over a computer network. The machine-learned classifier is stored. For example, after creation, the machine-learned network includes one or more layers with values for various learnable parameters, such as convolution kernels, down sampling weights, and/or connections. The values of the parameters and/or the networks as trained are stored. The machine-learned networks are stored in a memory, such as memory of the machine or the database with the examples. The machine-learned network may be transmitted to a different memory. The machine-learned network may be duplicated for application by other devices or machines, such as processors of x-ray scanners. The memories of x-ray or other scanners may store copies of the machine-learned network for application for specific patients.

In act 18, the machine-learned model is applied. A processor or computer applies the model to a patient image with or without clinical data for a patient. The same or different machine used to train applies the model.

To apply, the patient image, such as from an x-ray scan of the patient, is applied with or without other data (e.g., clinical data) as input to the machine-learned model. In response, the machine-learned model outputs a classification of the patient image. The classification may be a detection of one or more types of abnormalities. One available class may be no abnormality. The patient image is classified as including or not including one or more different types of abnormalities. The patient has or does not have one or more different types of abnormalities. The machine-learned classifier, having been trained to classify based on noise and/or correlation regularization, classifies the input image and/or data. The patient is imaged, and the resulting image is classified using the machine-learned model.

An image showing results of the application may be generated. The image may be color coded, annotated, or labeled to indicate the classification. The image may be of the classification or of the classification with a representation of the anatomy (e.g., chest radiograph with an annotation showing the classification for the image or by region of the image). The classification may be added to the patient record.

The noise and correlation regularization improve performance of the machine-learned model in classification. For the chest radiographs with five abnormalities with the noise levels of Table 1 and the correlations of FIG. 3, a neural network is trained with equation 1 as a baseline loss, with equation 2 for noise regularization, and with equation three for correlation regularization. Table 2 shows the area under the curve scores for the resulting machine-learned models.

TABLE 2

|  | Effusion | Cardiomegaly | Consolidation | Atelectasis | Mass |
|---|---|---|---|---|---|
| Baseline $\mathcal{L}_{Abn}$ | 0.923 | 0.926 | 0.812 | 0.821 | 0.804 |
| Prior label noise $\mathcal{L}_{Noise}$ | 0.940 | 0.927 | 0.836 | 0.845 | 0.829 |
| Label correlation $\mathcal{L}_{Corr}$ | 0.915 | 0.940 | 0.831 | 0.831 | 0.838 |

The performance and generalizability of the detection and classification system is increased. The robustness against label noise is increased based on loss regularization. These improvements are achieved by the regularization components that avoids generating over-confident systems by regularization components applied on the loss function. The knowledge about label noise for each abnormality is increased. The expert reading procedure leads to noise ratios between original and expert labels. The received label noise ratios help to analyze interpretation difficulties of different abnormalities in chest radiograph assessment. The training time may be decreased due to regularization. A baseline classification loss is extended with one or two regularization components to deal with label noise. Prior label noise probabilities and abnormality correlation information is integrated, which increases the accuracy of the classification system FIG. 4 shows a block diagram of one embodiment of arrangement including a system 40 for machine training for abnormality classification and a system 45 for abnormality detection in medical imaging. Using noise, correlation, and/or other regularization, the system 40 for training trains the machine learning model 44 with the noisy training data 42. The resulting machine-learned model 48, having been previously trained with the regularization, is used by the system 45 for application to a patient.

The systems 40, 45 are two separate systems. The only shared component is the final machine learning model 44 of the system 40 for training being copied and/or used as the machine-learned model 48 of the system 45 for detection. In alternative embodiments, one or more components are shared, such as the memories 41 and 50 being the same memory and/or the processors 43, 47 being the same processor. One system 40, 45 may be provided without the other system 45, 40.

The system 40 for training includes the memory 41 and the processor 43. The memory 41 is for storing the training data 42 and/or the machine learning model 44, such as storing the defined architecture of the model and values for the learnable parameters. The processor 43 is for machine learning. Additional, different, or fewer components may be provided. For example, a network or network connection is provided, such as for networking the memory 41 with the processor 43. As another example, a user interface or user input device is provided with the processor 43 for defining the machine learning model 44, controlling training, and/or obtaining the training data 42.

The memory 41 and processor 43 are part of a server, workstation, or computer. The memory 41 is part of the computer associated with the processor 43 or is a separate or remote database for access over a computer network, such as being in a cloud hosted electronic health record or electronic medical records system.

The system 45 for detection includes one or more medical imagers 46, the processor 47, the memory 50 (e.g., a medical records database), and a display 49. Additional, different, or fewer components may be provided. For example, a user interface or input device is provided on the medical imager 46 and/or for the processor 47. In another example, a network or network connection is provided, such as for networking different components (e.g., medical imager 46 with the processor 47 and/or the processor 47 with the memory 50).

The memory 50, processor 47, and/or display 49 are part of a server, workstation, or computer. In one embodiment, the memory 50, processor 47, and/or display 49 are a server or workstation. The memory 50 may be part of a same computer or a separate computer from the processor 47, such as being in a cloud hosted electronic health record or electronic medical records system. The medical imager 46 and the processor 47 are at different facilities, such as being remote from each other, or at a same facility. Alternatively, the processor 47 is part of or at a same facility (i.e., local to) the medical imager 46.

The memories 41 and 50 are a random-access memory, system memory, cache memory, hard drive, optical media, magnetic media, flash drive, buffer, database, combinations thereof, or other now known or later developed memory device for data. The memory 41 stores the training data 42, loss data, regularization data, and/or the machine learning model 44. For example, images of anatomy and ground truth classifications for the images are stored as the training data 42. In one embodiment, the training data 42 is x-ray images, such as chest radiographs. The memory 50 stores patient information (e.g., image or images and clinical data), the machine-learned model 48, and/or output detections.

The memories 41, 50 or other memories are alternatively or additionally non-transitory computer readable storage media storing data representing instructions executable by the programmed processor 43, the programmed processor 47, and/or medical imager 46. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, tensor processing unit (TPU), neural processing unit, AI accelerator, or system.

The processors 43, 47 are general processors, control processors, digital signal processors, application specific integrated circuits, field programmable gate arrays, GPUs, AI accelerators, neural processing units, TPUs, or other hardware processors for machine training the model 44 and/or for applying the machine-learned model 48. In one embodiment, the processor 43 is part of a computer, workstation, server, or other device configured to machine train. The processor 47 is part of a computer, workstation, server, or other device configured to apply image processing and/or apply the machine-learned model 48 for a given patient. The processors 43, 47 may be networks of computing devices, such as multiple computers or servers. The processors 43, 47 are configured by software, hardware, and/or firmware.

The processor 43 is configured to machine train from the training data 42. The machine training includes calculation of loss with a noise and/or correlation regularization. Noise in the labels for an abnormality and/or between abnormalities is countered by use of the regularization. An expert reading study and/or correlation of abnormalities and comorbidity are used to determine weights, functions, or other aspects of the regularization. The machine training with the regularized loss results in the machine-learned classifier or model 44. This trained model 44 or a copy is provided to the system 45 for detection as the machine-learned model 48.

For application to a given patient, the medical imager 46 scans the patient and/or a stored image or images from previous scans are loaded from the memory 50. The medical imager 46 is a MR, CT, x-ray, ultrasound, nuclear medicine (e.g., PET or SPECT), or another scanner. In other embodiments, the medical imager 46 is a multi-modality device, such as a combination of nuclear medicine and x-ray or CT. In yet other embodiments, invasive, other non-invasive, or minimally invasive imaging systems are used.

The medical imager 46 is configured to scan or image a patient. The same imager 46 may be used to scan different patients at different times. Other imagers 46 may be used to scan other patients. The medical imager 46 is configured to output scan data to the processor 47, memory 50, and/or display 49. The scan data is data resulting from the scan at any stage of processing. For example, an image generated from the scan is provided. For an x-ray system, the image may be a chest radiograph. The medical imager 46 provides image data as scan data resulting from scanning with any amount of processing towards generating an image. The image data may be formatted for display, such as RGB values, or may be in a scan format (e.g., scalar values).

The processor 47 is configured to apply the machine-learned model 48 to the image of the patient. The machine-learned model 48 was trained with noise and/or correlation regularization to detect an abnormality in the image. The noise regularization accounted for noise in ground truth labels of the training data 42 for any given abnormality used in machine training. The correlation regularization accounted for mischaracterization between different types of abnormalities of the training data 42 used in machine training. The processor 47 is configured to apply the machine-learned model 48 to the scan data with or without other data (e.g., clinical data for the patient).

The display 49 is a monitor, LCD, projector, plasma display, CRT, printer, or other now known or later developed device for displaying an image of the classification of the patient as having or not having one or more abnormalities based on the detection from the application. The display 49 is at the medical imager 46, the processor 47, a physician's computer, or another location. The display 49 receives the output from the processor 47, medical imager 46, or memory 50. The processor 47 formats the data for display (e.g., mapping to RGB values) and stores the image in a buffer, configuring the display 49. The display 49 uses the image in the buffer to generate an image for viewing.

The output from the machine-learned model 48 is displayed. The classification may be indicated along with an image of anatomy. The image includes graphics, alphanumeric text, anatomical scan, coded spatial representation of anatomy, and/or combinations showing the classification with or without also showing anatomy or the medical image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for machine learning abnormality assessment in medical imaging by a machine, the method comprising:
    obtaining training data comprising medical images and ground truth labels for the medical images, the ground truth labels designating an abnormality represented by the medical images;
    machine training, by the machine, a model from the training data, the machine training using a loss function, the loss function including a regularization, the regularization comprising a noise regularization, where the noise regularization includes a predetermined function of prior label noise probabilities; and
    storing the model resulting from the machine training in a memory.

2. The method of claim 1 wherein machine training comprises machine training with the loss function comprising a cross-entropy function comparing a classification of abnormality output of the model with the ground truth labels.

3. The method of claim 1 where machine training comprises machine training with the ground truth labels comprising binary labels for absence or presence of the abnormality and the loss function being weighted as a function of number of positive and number of negative instances of the abnormality in the medical images of the training data.

4. The method of claim 1 further comprising measuring a noise level of the ground truth labels, and wherein machine training comprises machine training with the noise regularization being a function of the noise level.

5. The method of claim 4 wherein the noise level comprises a specificity and a sensitivity of the ground truth labels for the abnormality, and wherein the noise regularization comprises a first weight that is a function of the specificity and a second weight that is a function of the sensitivity.

6. The method of claim 1 wherein the noise regularization comprises an inverse binary cross-entropy function.

7. The method of claim 1 wherein the ground truth labels designate at least first and second types of abnormalities, and wherein machine training comprises machine training with the regularization of the loss function further comprises a correlation regularization, the correlation regularization correlating the ground truth labels for the first type of abnormality to the ground truth labels for the second type of abnormality.

8. The method of claim 7 wherein the correlation regularization comprises a covariance.

9. The method of claim 8 wherein the at least first and second types of abnormalities comprise at least four types of abnormalities, and wherein machine training comprises machine training with the correlation regularization as a sum of the covariance between all of the at least four types of abnormalities.

10. The method of claim 1 wherein machine training comprises machine training with the regularization comprising both the noise regularization and a correlation regularization.

11. The method of claim 1 wherein obtaining comprises obtaining the medical images of the training data as chest radiographs and wherein the abnormality comprises effusion, cardiomegaly, consolidation, atelectasis, and/or mass.

12. The method of claim 1 further comprising applying the model resulting from the machine training to a patient image for a patient, the applying outputting a classification of the patient image has having or not having the abnormality.

13. A system for abnormality detection in medical imaging, the system comprising:
a medical imaging system configured to generate an image of a patient;
a processor configured to apply a machine-learned model to the image of the patient, the machine-learned model having been trained with a noise regularization to detect an abnormality in the image, where the noise regularization includes a predetermined function of prior label noise probabilities; and
a display configured to display a classification of the patient as having or not having the abnormality based on the abnormality detection.

14. The system of claim 13 wherein the noise regularization accounting for noise in ground truth labels used in machine training.

15. The system of claim 13 wherein the processor is configured to apply the machine-learned model having been trained with a correlation regularization accounting for mischaracterization between different types of abnormalities.

16. The system of claim 13 wherein the medical imaging system comprises an x-ray system and wherein the noise regularization is for ground truth labels for abnormalities in x-ray images.

17. A system for machine training for abnormality classification, the system comprising:
a memory configured to store training data including images of anatomy and ground truth classifications for the images and to store a machine-learned classifier; and
a processor configured to machine train from the training data, the machine training including calculation of loss with a noise regularization, label noise probabilities, and the machine training with the calculation of loss resulting in the machine-learned classifier.

18. The system of claim 17 wherein the processor is further configured to machine train with a correlation regularization.

19. The system of claim 17 wherein the processor is further configured to:
measure a noise level of the ground truth labels; and
machine train with the noise regularization being a function of the noise level.

20. The system of claim 17 wherein the noise regularization comprises an inverse binary cross-entropy function.

* * * * *